(12) United States Patent
El-Khouly

(10) Patent No.: US 11,681,503 B2
(45) Date of Patent: Jun. 20, 2023

(54) MACHINE LEARNING VISUAL CODE AND ACTION GENERATION

(71) Applicant: INTERNATIONAL BUSINESS MACHINES CORPORATION, Armonk, NY (US)

(72) Inventor: Ahmed Hussein Mohamed Kamel El-Khouly, Kanata (CA)

(73) Assignee: International Business Machines Corporation, Armonk, NY (US)

( * ) Notice: Subject to any disclaimer, the term of this patent is extended or adjusted under 35 U.S.C. 154(b) by 161 days.

(21) Appl. No.: 17/302,220

(22) Filed: Apr. 27, 2021

(65) Prior Publication Data

US 2022/0342643 A1   Oct. 27, 2022

(51) Int. Cl.
  *G06F 8/34* (2018.01)
  *G06N 20/00* (2019.01)
  *G06F 16/21* (2019.01)
  *A61B 5/00* (2006.01)

(52) U.S. Cl.
  CPC .............. *G06F 8/34* (2013.01); *G06F 16/219* (2019.01); *G06N 20/00* (2019.01); *A61B 5/4504* (2013.01)

(58) Field of Classification Search
  CPC .......... A61B 5/4504; G06N 20/00; G06F 8/34
  See application file for complete search history.

(56) References Cited

U.S. PATENT DOCUMENTS

| 10,905,336 | B1* | 2/2021 | Moon | A61B 5/4504 |
| 2014/0114907 | A1* | 4/2014 | Kozina | G06F 16/219 |
| | | | | 707/602 |
| 2019/0188333 | A1 | 6/2019 | Williams | |
| 2019/0317748 | A1* | 10/2019 | Dawson | G06N 20/00 |

OTHER PUBLICATIONS

Kim Sung et al, KR 20090004216, "System and Method for Classifying Named Entities From Speech Recognition",(translation), Jan. 12, 2009, 14 pgs <KR_20090004216.pdf>.*
Mell, Peter et al.; "The NIST Definition of Cloud Computing;" National Institute of Standards and Technology; Special Publication 800-145; Sep. 2011; 7 pages.

(Continued)

*Primary Examiner* — Tuan A Vu
(74) *Attorney, Agent, or Firm* — Schmeiser, Olsen & Watts, LLP; David Mattheis

(57) ABSTRACT

A method, system, and computer program product for implementing machine learning visual code and action generation is provided. The method includes receiving from a plurality of hardware and software sources, digital description data associated with visual presentations and an action for execution. A resulting code-based class for each portion of the digital description data is generated with respect to the visual presentation. Self learning software code is executed and a type of visual presentation is selected with respect to associated visual features and the code-based class. Additionally, a visual presentation is selected and an action is executed resulting in hardware and software of a server hardware device being operationally modified. The visual presentation is presented to a user.

18 Claims, 13 Drawing Sheets

(56) References Cited

OTHER PUBLICATIONS

Anonymous; System & method for recommending visualizations in data and result sets, utilizing context; ip.com; IPCOM000255221D; Sep. 11, 2018; 5 pages.

Anonymous; Visualization recommendation system using a hybrid machine learning approach; ip.com; IPCOM000260192D; Oct. 30, 2019; 4 pages.

Fulton, Kelsey et al.; Towards a Customizable Framework for Evaluating Visualization Recommendations; https://www.cs.umd.edu/sites/default/files/scholarly_papers/fulton_scholarly_paper.pdf; 2019; 10 pages.

Hu, Kevin Z. et al; VixML: A Machine Learning Approach to Visualization Recommendation; arXiv: 1808.04819v1; Aug. 14, 20118; 14 pages.

Qian, Xin et al.; ML-based Visualization Recommendation: Learning to Recommend Visualizations from Data; arXiv; 2009.12316v1; Sep. 25, 2020; 17 pages.

Van Hasselt et al., Deep Reinforcement Learning with Double Q-Learning, AAAI'16: Proceedings of the Thirtieth AAAI Conference on Artificial Intelligence, Feb. 2016, pp. 2094-2100.

Vartak, Manaxi et al.; SEEDB: Efficient Data-Driven Visualization Recommendations to Support Visual Analytics Proceedings of VLDB Endowment, vol. 8, No. 13; Sep. 2015; pp. 2182-2193.

Ziyu Wang, et al., Dueling Network Architectures for Deep Reinforcement Learning, arXiv:1511.06581v3 [cs.LG] Apr. 5, 2016.

\* cited by examiner

MACHINE LEARNING VISUAL CODE AND ACTION GENERATION

BACKGROUND

The present invention relates generally to a method for automating machine learning visual code and action generation and in particular to a method and associated system for improving software technology associated with selecting visual presentations with respect to a type, executing an associated action resulting in hardware and software of a server hardware being operationally modified, and presenting the selected visual presentations.

SUMMARY

A first aspect of the invention provides a machine learning visual code and action generation method comprising: receiving, by a processor of a server hardware device from a plurality of hardware and software sources, digital description data associated with visual presentations and an associated action for execution; generating by the processor in response to the receiving the digital description data, a code based class for each portion of the digital description data with respect to the visual presentation; executing, by the processor, self-learning software code; selecting, by the processor in response to the executing the self-learning software code, a type of visual presentation associated with the visual presentations with respect to associated visual features and the code based class; selecting, by the processor, a visual presentation of the visual presentations with respect to the type of visual presentation; executing, by the processor, the action resulting in hardware and software of the server hardware device being operationally modified; and presenting, by the processor to the user via a hardware and software interface, the visual presentation.

A second aspect of the invention provides a computer program product, comprising a computer readable hardware storage device storing a computer readable program code, the computer readable program code comprising an algorithm that when executed by a processor of a server hardware device implements a machine learning visual code and action generation method, the method comprising: receiving, by the processor from a plurality of hardware and software sources, digital description data associated with visual presentations and an associated action for execution; generating by the processor in response to the receiving the digital description data, a code based class for each portion of the digital description data with respect to the visual presentation; executing, by the processor, self-learning software code; selecting, by the processor in response to the executing the self-learning software code, a type of visual presentation associated with the visual presentations with respect to associated visual features and the code based class; selecting, by the processor, a visual presentation of the visual presentations with respect to the type of visual presentation; executing, by the processor, the action resulting in hardware and software of the server hardware device being operationally modified; and presenting, by the processor to the user via a hardware and software interface, the visual presentation.

A third aspect of the invention provides a server hardware device comprising a processor coupled to a computer-readable memory unit, the memory unit comprising instructions that when executed by the computer processor implements a machine learning visual code and action generation method comprising: receiving, by the processor from a plurality of hardware and software sources, digital description data associated with visual presentations and an associated action for execution; generating by the processor in response to the receiving the digital description data, a code based class for each portion of the digital description data with respect to the visual presentation; executing, by the processor, self-learning software code; selecting, by the processor in response to the executing the self-learning software code, a type of visual presentation associated with the visual presentations with respect to associated visual features and the code based class; selecting, by the processor, a visual presentation of the visual presentations with respect to the type of visual presentation; executing, by the processor, the action resulting in hardware and software of the server hardware device being operationally modified; and presenting, by the processor to the user via a hardware and software interface, the visual presentation.

The present invention advantageously provides a simple method and associated system capable of automating machine learning visual code and action generation.

DETAILED DESCRIPTION

Figure 1:
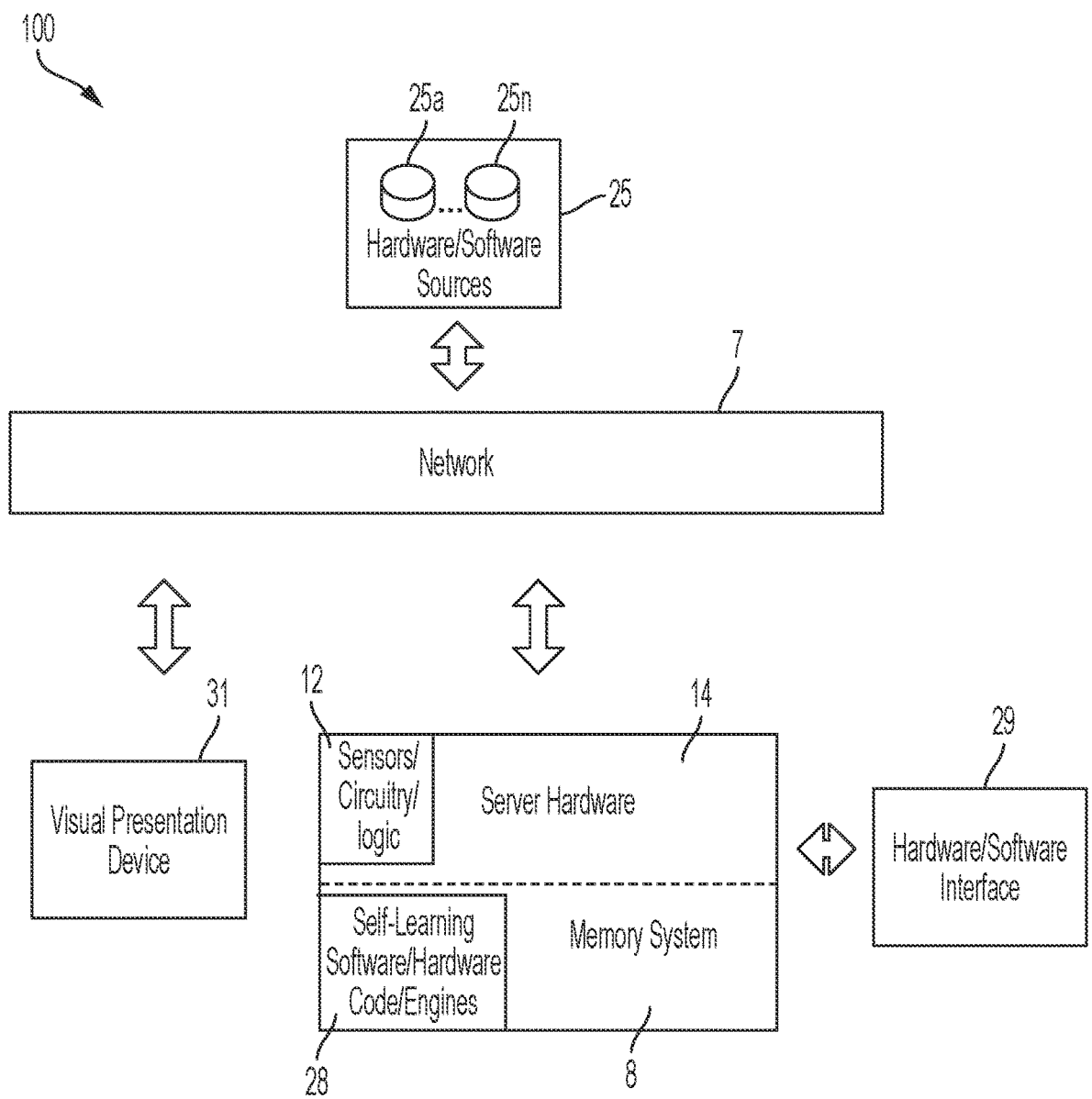
FIG. 1 illustrates a system for improving software technology associated with selecting visual presentations with respect to a type, executing an associated action resulting in hardware and software of a server hardware being operationally modified, and presenting the selected visual presentations, in accordance with embodiments of the present invention.

FIG. 1 illustrates a system 100 for improving software technology associated with selecting visual presentations with respect to a type, executing an associated action resulting in hardware and software of a server hardware being operationally modified, and presenting the selected visual presentations, in accordance with embodiments of the present invention. A visual presentation may include any type of visual presentation including, inter alia, a video presentation, a video streaming presentation, a visual pictorial presentation presented via an interface, etc. Typical data visualization processes are implemented with respect to data analytics for representing trends, relationships, and patterns in a visual format accessible for analysis. However, selecting a chart applicable to represent data may involve a complicated process if a user does not know any associated data characteristics (e.g., metadata). Therefore system 100 is configured to execute a code implemented process for recommending charts and columns with respect to slot bindings for user a selected set of columns thereby allowing a user to study and analyze data from a different angle. Likewise, system 100 is configured to digitally bind columns to suitable slots for a given chart. Determined slot to column compatibility is assigned a score and a recommender component will optimize an overall binding score. Subsequently, charts may be ranked based on an overall binding score. A related binding compatibility is measured by comparing column features (e.g., ontology, concepts, statistics, logical groups, etc.) with slot specifications for a specific chart. Therefore, system 100 is configured to:

1. Execute column to slot binding and chart recommendation processes.
2. Ensures a consistency of recommendations and binding.
3. Reduce hand crafted code to perform column to slot binding.

System 100 enables support for two application programming interfaces (API): a visualization recommendation API and a binding recommendation API. A visualization recommendation API analyzes a set of columns and recommends best charts with column to slot bindings (i.e., best representing the columns). A binding recommendation API is configured to recommend bindings for unbound columns (based on a specific chart and a set of bound and unbound columns). Likewise, system 100 is configured to recommend bindings for unbound columns. System 100 enables a process for automatically executing the aforementioned APIs via a single machine learning model without the use of hand-crafted code. The recommendation API is configured to generate recommendations associated with column to slot bindings for candidate charts and generate associated recommendation charts comprising a highest overall binding score. The binding API is configured to generate recommendations associated with best bindings for unbound columns for a given chart. Therefore, system 100 comprises a complete visualization recommendation system for recommending bindings and associated visualizations thereby ensuring a consistency and correctness of recommendations and providing improved bindings. Additionally, system 100 is configured to be fully implemented with respect to client hardware with a minimal amount of application code.

System 100 of FIG. 1 includes server hardware 14, hardware/software sources 25, a visual presentation device 31, and a hardware/software interface 29 interconnected through a network 7. Server hardware 14 comprises sensors/circuitry/logic 12 and a (specialized) memory system 8. Memory system 8 comprises self-learning software/hardware code/engines 28 including executable code. Memory system 8 may include a single memory system. Alternatively, memory system 8 may include a plurality of memory systems. Hardware/software sources 25 comprise remote source systems (e.g., media such as news sources, Internet information sources, social media sources, visual storage systems, etc.) and may include databases 25a . . . 25n. Server hardware 14, hardware/software sources 25, visual presentation device 31, and hardware/software interface 29 each may comprise an embedded device(s). An embedded device is defined herein as a dedicated device or computer comprising a combination of computer hardware and software (fixed in capability or programmable) specifically designed for executing a specialized function. Programmable embedded computers or devices may comprise specialized programming interfaces. In one embodiment, server hardware 14, hardware/software sources 25, visual presentation device 31, and hardware/software interface 29 may each comprise a specialized hardware device comprising specialized (non-generic) hardware and circuitry (i.e., specialized discrete non-generic analog, digital, and logic-based circuitry) for (independently or in combination) executing a process described with respect to FIGS. 1-13. The specialized discrete non-generic analog, digital, and logic-based circuitry (e.g., sensors/circuitry/logic 12, etc.) may include proprietary specially designed components (e.g., a specialized integrated circuit, such as for example an Application Specific Integrated Circuit (ASIC) designed for only implementing an automated process for improving software technology associated with selecting visual presentations with respect to a type, executing an associated action resulting in hardware and software of a server hardware being operationally modified, and presenting the selected visual presentations. Sensors/circuitry/logic 12 may include any type of internal or external sensors including, inter alia, GPS sensors, Bluetooth beaconing sensors, cellular telephone detection sensors, Wi-Fi positioning detection sensors, triangulation detection sensors, activity tracking sensors, a temperature sensor, an ultrasonic sensor, an optical sensor, a visual retrieval device, humidity sensors, voltage sensors, network traffic sensors, etc. Network 7 may include any type of network including, inter alia, a local area network, (LAN), a wide area network (WAN), the Internet, a wireless network, etc.

System 100 is enabled to execute a visualization recommendation process via execution of deep reinforcement learning code as follows:

Generating digital presentation capabilities within an environment comprising a set of supported charts. The digital capabilities include: new episode creation, reward calculation and state transition, modeling a digital state comprising a chart type, slot bindings, and unbound columns, etc.

2. Generating an episode with an initial state in response to determining that an unbound column requires binding. The episode is generated with respect to an initial state comprising a chart type, features of bound columns set to proper slots, and an array of unbound features.

3. Selecting (from a first model) a first unbound column to define an action as a slot number. The first unbound column is bound to one slot.

4. Selecting (from a second model) a second unbound column to bind the unbound column to a slot.

5. Generating a vectored representation of features as an input to an agent reinforced model. Likewise, a selected best binding action is generated using an aggregate score of each binding (given an initial state) resulting in a reward and a new state.

6. Ranking each chart using a respective aggregate binding score for every chart.

Figure 2:
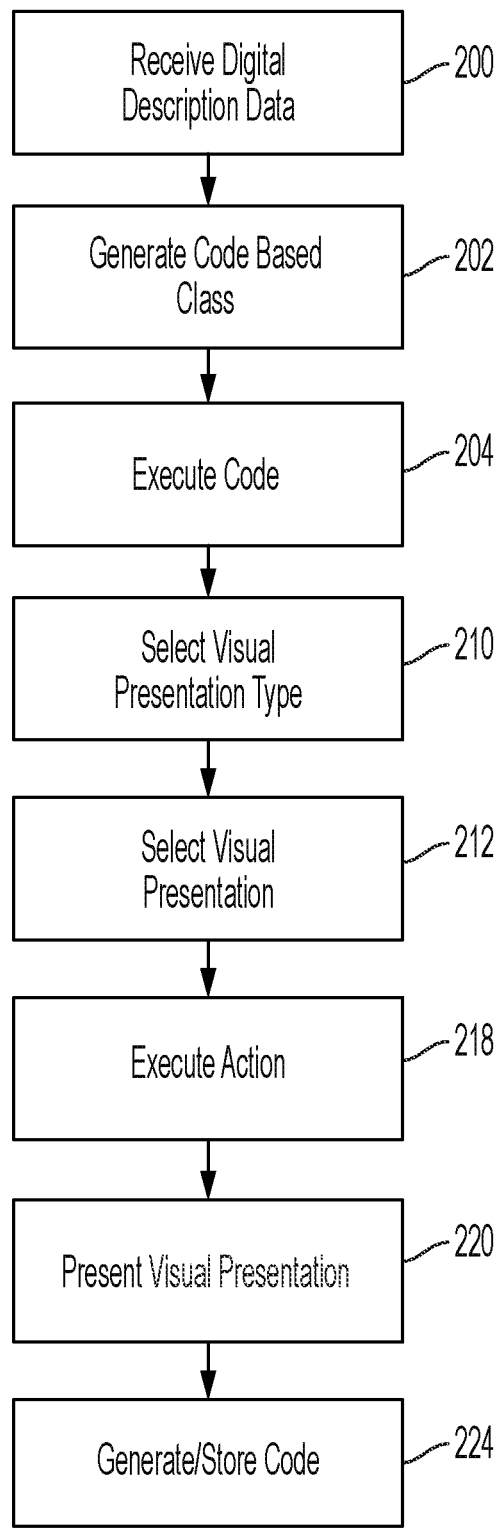
FIG. 2 illustrates an algorithm detailing a process flow enabled by the system of FIG. 1 for improving software technology associated with selecting visual presentations with respect to a type, executing an associated action resulting in hardware and software of a server hardware being operationally modified, and presenting the selected visual presentations, in accordance with embodiments of the present invention.

FIG. 2 illustrates an algorithm detailing a process flow enabled by system 100 of FIG. 1 for improving software technology associated with selecting visual presentations with respect to a type, executing an associated action resulting in hardware and software of a server hardware being operationally modified, and presenting the selected visual presentations, in accordance with embodiments of the present invention. Each of the steps in the algorithm of FIG. 2 may be enabled and executed in any order by a computer processor(s) executing computer code. Additionally, each of the steps in the algorithm of FIG. 2 may be enabled and executed in combination by server hardware 14, hardware/software sources 25, visual presentation device 31, and hardware/software interface. In step 200, digital description data is received (by a server) from a plurality of hardware and software sources. The digital description data is associated with visual presentations and an associated action for execution. The visual presentations are associated with user interface based graphical presentations. The digital description data describes names, hardware and software communication slots, and statistical and ontological concept features of the visual presentations. The ontological and statistical concept features are associated with a network-based dictionary of concept and statistical mapping code.

In step 202, a code-based class for each portion of the digital description data is generated with respect to visual presentation. The code-based class is configured to execute a software state transition for modifying operation of the server hardware device for executing the action.

In step 204, the self-learning software code is executed. In step 210, a type of visual presentation is selected in response to step 202. The type of visual presentation is associated with the visual presentations with respect to associated visual features and the code-based class. Selecting the type of visual presentation may include determining a software state change for representing the type of visual presentation associated with the visual presentations.

In step 212, a visual presentation is selected with respect to the selected type of visual presentation. In step 218, the action is executed resulting in hardware and software of the server hardware device being operationally modified. Executing the action may include: binding portions of the visual presentation and modifying the self-learning software code in response to results of the binding.

In step 220, the visual presentation is presented to a user via a hardware and software interface. In step 224, the self-learning software code for executing future processes associated with executing a machine learning visual code and action generation process. The self-learning software code is stored within a modified portion of a memory structure of the server hardware device.

Figure 3:
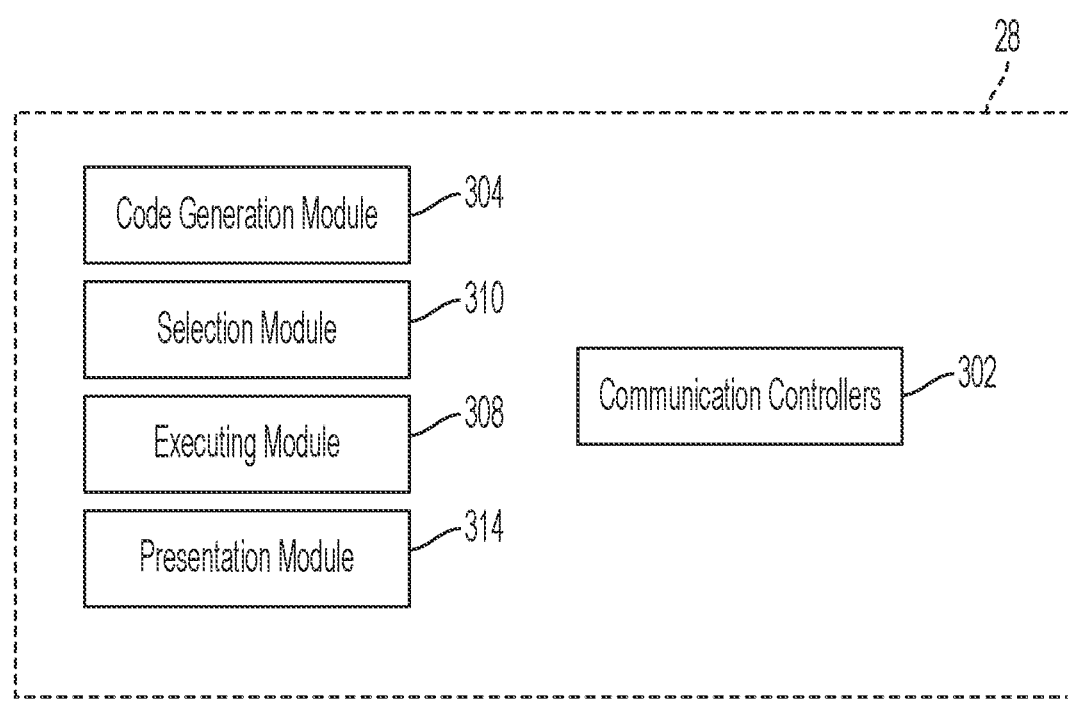
FIG. 3 illustrates an internal structural view of the self-learning software/hardware code/engine of FIG. 1, in accordance with embodiments of the present invention.

FIG. 3 illustrates an internal structural view of self-learning software/hardware code engines 28 of FIG. 1, in accordance with embodiments of the present invention. Self-learning software/hardware code/engines 28 includes a code generation module 304, a selection module 310, an executing module 308, a presentation module 314, and communication controllers 302. Code generation 304 comprises specialized hardware and software for controlling all functions related to generating code and code-based class. Selection module 310 comprises specialized hardware and software for controlling all functionality related to the selection steps described with respect to the algorithm of FIG. 2. Executing module 308 comprises specialized hardware and software for controlling all functions related to the execution steps of FIG. 2. Presentation module 314 comprises specialized hardware and software for controlling all functions related to the visual presentation steps of the algorithm of FIG. 2. Communication controllers 302 are enabled for controlling all communications between code generation module 304, selection module 310, executing module 308, and presentation module 314.

Figure 4:
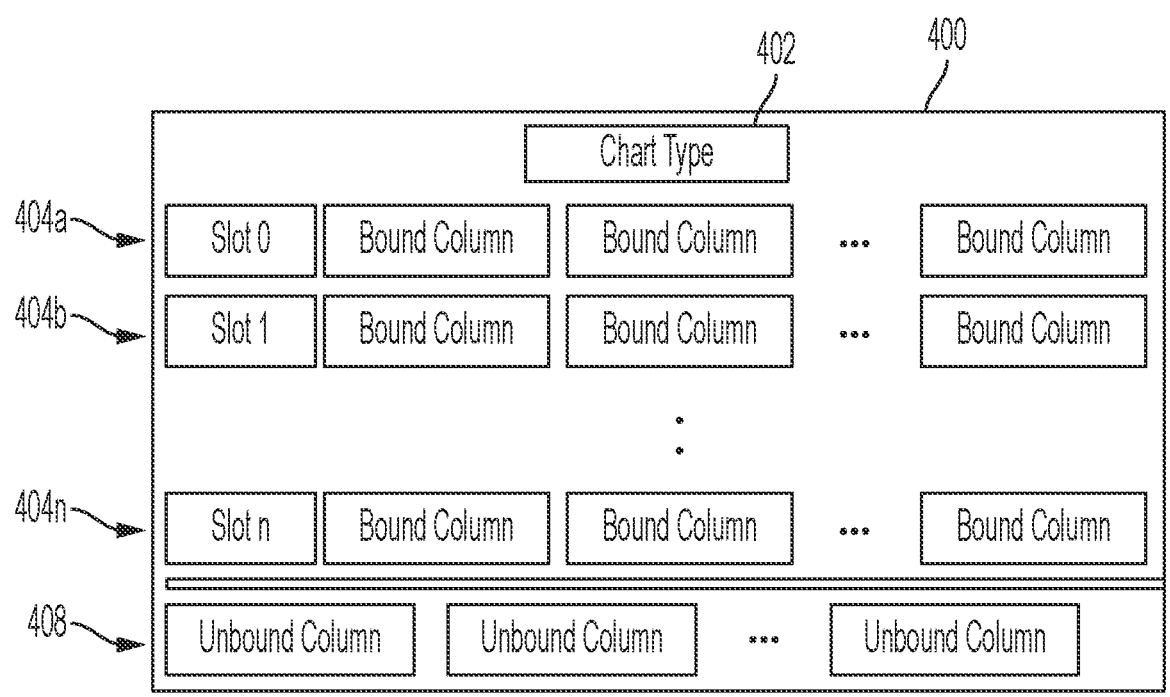
FIG. 4 illustrates a Markov Chain Process (MCP) component executing column to slot binding, in accordance with embodiments of the present invention.

FIG. 4 illustrates a Markov Chain Process (MCP) component 400 executing column to slot binding, in accordance with embodiments of the present invention. A binding problem is mapped as an MCP. In response, reinforced learning algorithms are executed to enable a recommender system thereby casting binding columns to chart slots with respect to an episodic environment such that every episode is concluded when all columns are bound to the chart. MCP component comprises a chart type component 402, slot binding components 404a . . . 404n, and unbound column components 408. Chart type component 402 is configured to execute hot encoding code with respect to a chart. Slot binding components 404a . . . 404 comprise an array of feature vectors representing columns placed within a slot. A feature vector comprises a binary representation of features column extracted features (e.g., ontology concepts, statistics, usage, etc.). Unbound column component 408 comprises an array of feature vectors representing columns to be bound.

Figure 5:
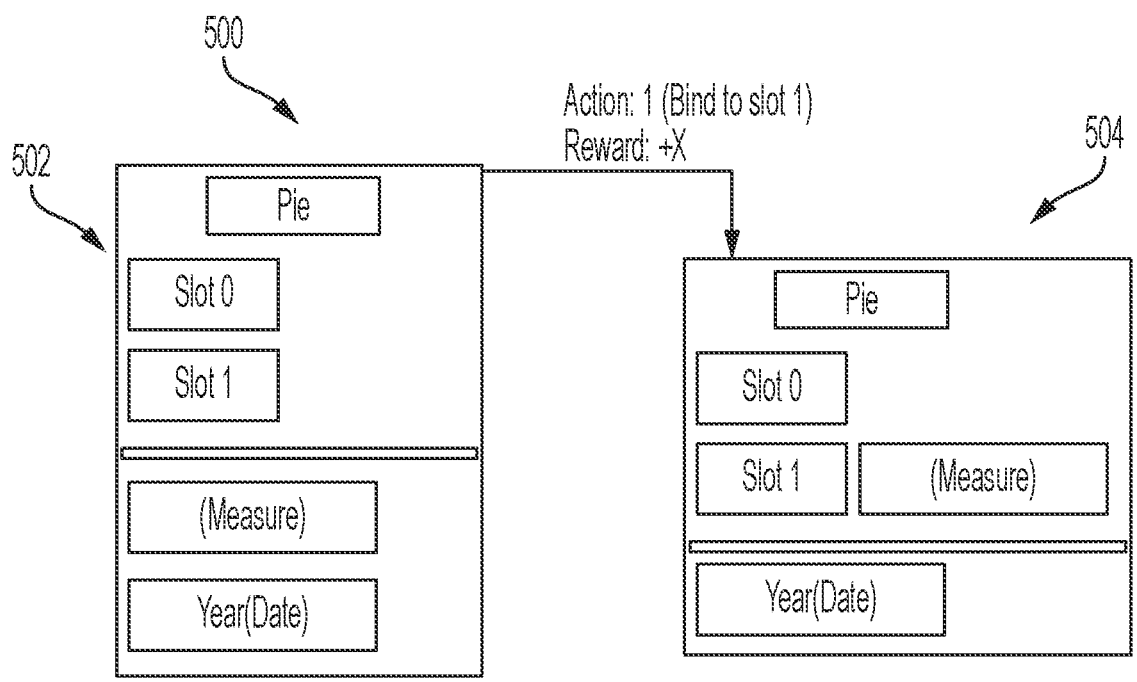
FIG. 5 illustrates a modeled action enabled by system 100 of FIG. 1, in accordance with embodiments of the present invention.

FIG. 5 illustrates a modeled action 500 enabled by system 100 of FIG. 1, in accordance with embodiments of the present invention. Modeled action 500 is associated with an unbound column selection. For example, a first unbound column 502 may be selected and inputted into a valid slot for given charts. An associated environment may comprise a set of supported charts 504. The associated environment is associated with the following functionalities:

1. Generating new episode code for implementing a process for generating binding scenarios by uniformly and randomly selecting a chart, a number of columns, and a set of columns (and column features). The new episode code initiates with an initial state representing a selected scenario. The new episode code continues until all slots are bound within a terminal state.

2. Generating reward code with respect to a given state and action. Each associated chart comprises an associated reward that asses an action executed within a given state and returns a numeric representation of the reward (i.e., positive or negative). The reward code may be generated automatically from chart descriptors specifying chart slots in terms of allowed features.

3. Executing a state transition process with respect to a state and an action.

Modeled action 500 is enabled by a software/hardware agent executing a reinforced learning algorithm for predicting a binding action for unbound columns with respect to an associated slot and receiving a reward from an associated software/hardware environment. During a training process the software/hardware agent is configured to learn from a reward returned from the software/hardware environment.

Figure 6:
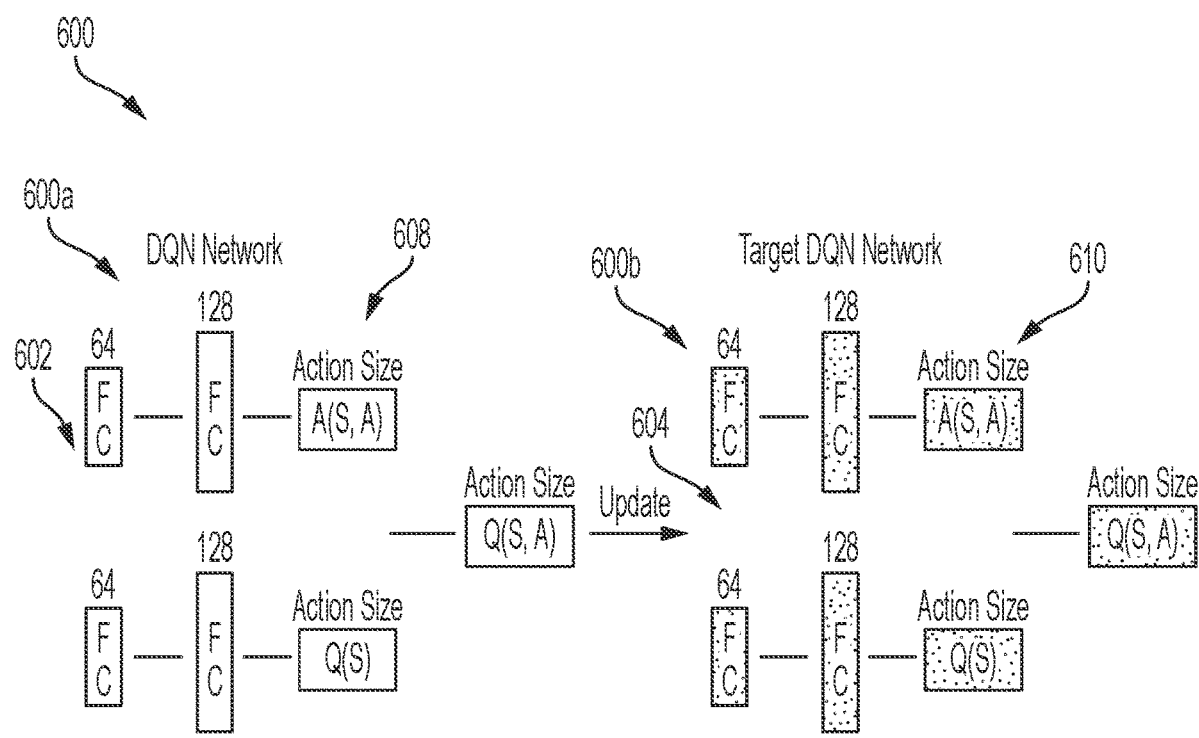
FIG. 6 illustrates a deep learning network architecture for generating chart and associated bindings, in accordance with embodiments of the present invention.

FIG. 6 illustrates a deep learning network architecture 600 for generating chart and associated bindings, in accordance with embodiments of the present invention. Deep learning network architecture 600 is associated with two analysis portions: a value calculation and advantage calculation. Deep learning network architecture 600 comprises a dual deep quality network architecture comprising a DQN network 600a and a target DQN network 600b for calculating a value of target states. DQN network 600a comprises fiber channels (FC) 602 and action code 608. Target DQN network 600b comprises fiber channels (FC) 604 and action code 610. Associated weights of target DQN network 600b are updated with respect to a specified number of steps executed by DQN network 600a executed during a training process. Dueling architecture enables a Q-value for an action within a state to be calculated as: $Q(S,A)=A(S,A)+Q(S)$. Likewise, a Bellman equation may be approximated as: $Qt(S,A)=R(S,A)+gamma*Qt(Sn, argmax(Q(Sn, A)))$ such that:

1. Qt comprises a target Q-value of an action taken in a state.
2. Sn comprises a next state following taken and an action in state S.
3. R comprises a reward given by the software/hardware environment for executing an action in a specific state.
4. Gamma comprises a discounting factor.

Deep learning network architecture 600 executed code for modelling an action advantage denoted by: $A(S,A)$ such that a first unbounded column is selected as follows:

An (software/hardware implemented) action is defined as a slot number where a first unbound column is bound to a first slot and a model is configured to predict an advantage of executed the action. Therefore, a number of possible actions (e.g., an action size) are equal to a maximum number of slots within all charts thereby configuring a model associated with a small number of actions (e.g., associated with charts comprising less than 10 slots) resulting in faster convergence and execution.

Subsequently, an unbound column is selected such that a software/hardware agent selects any unbound column and binds it to a slot. In this case, an action size is equal to max number of slots*max number columns thereby enabling a model to select bindable columns first and reject binding of remaining columns. A resulting episode is created with an initial state comprising a chart type, features of bound columns set to proper slots, and array of unbound features. A vectored representation is subsequently provided as an input to the agent and reinforced model configured to select a best binding action given an associated state resulting in a reward and associated new state. The aforementioned sequence will continue until all columns are bound. An aggregate score for each binding may represent a benefit of an overall chart.

For every chart supported by the software/hardware environment, an episode is created with an initial state associated with the aforementioned chart. All charts are subsequently ranked based on an aggregate binding score for every chart. A subset of charts may be used as an optimization candidate based on a charts capacity/number of mandatory slots thereby eliminating unsuitable charts.

Figure 7:
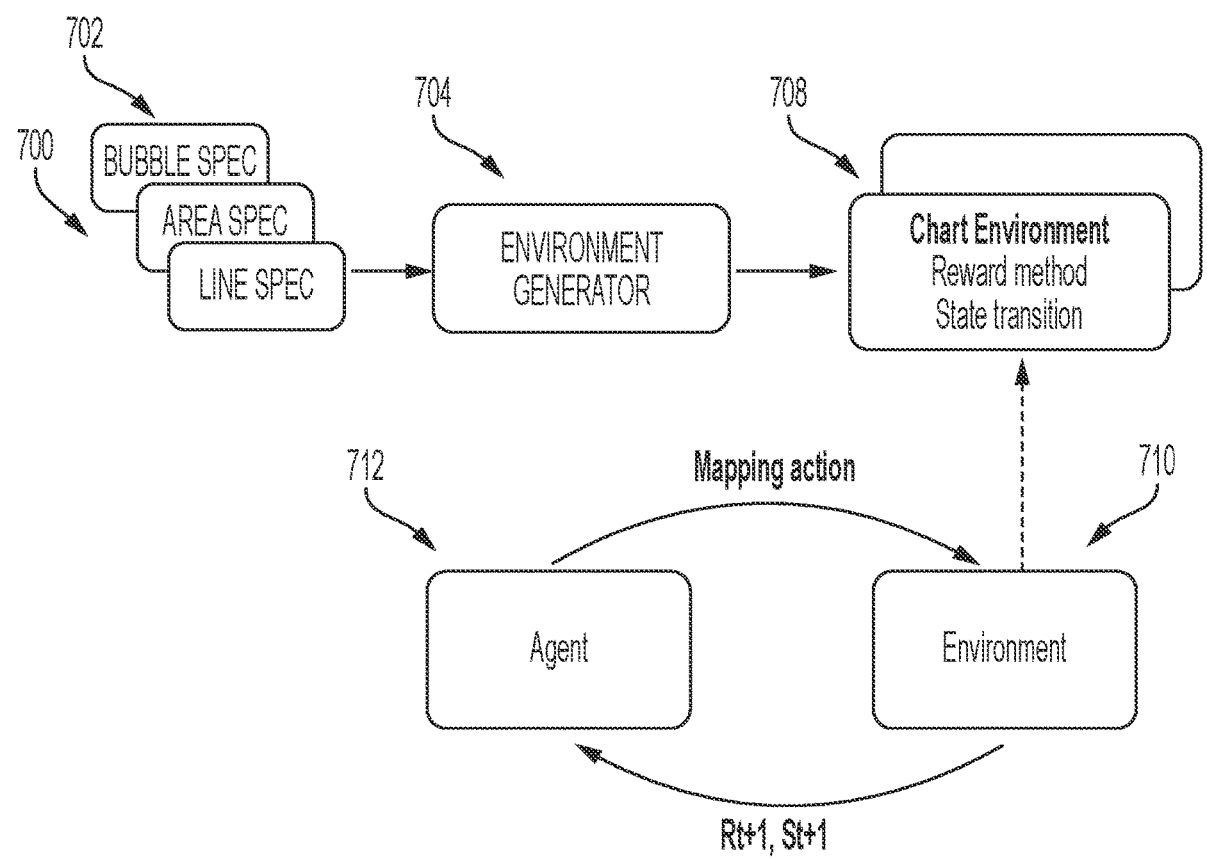
FIG. 7 illustrates a visual code training system, in accordance with embodiments of the present invention.

FIG. 7 illustrates a visual code training system 700, in accordance with embodiments of the present invention. Visual code training system 700 enables reward-based code to be automatically generated from chart descriptors such that visual code training system 700 may be easily extensible and new charts may be added without excessive development efforts. A training process executed with respect to visual code training system 700 is described as follows:

The process is initiated when chart descriptions 702 are provided as input to visual code training system 700. Chart descriptions 702 are described in a high-level software language specifying a chart name, slots, statistical, and ontological concept features for each column. The Ontological and statistical characteristics may be extended by providing a supplementary dictionary of concept/statistics mappings. Subsequently, an environment generator component 704 executes code for generating a chart environment class 708 for each provided chart descriptor. Chart environment class 708 enables a standard reward calculation and state transition for operating with respect to any provided chart in a standard manner. During the training process (for each training episode) and software hardware environment 710 uniformly selects code with respect to a random chart environment (e.g., a chart type) and additionally selects random columns (features) to be bound. Software/hardware environment 710 is configured to calculate a state representation for selected chart and columns. A visualization agent 712 is configured to execute actions (e.g., binding a column to a slot) for which software/hardware environment 710 responds with a reward and next state.

Figure 8:
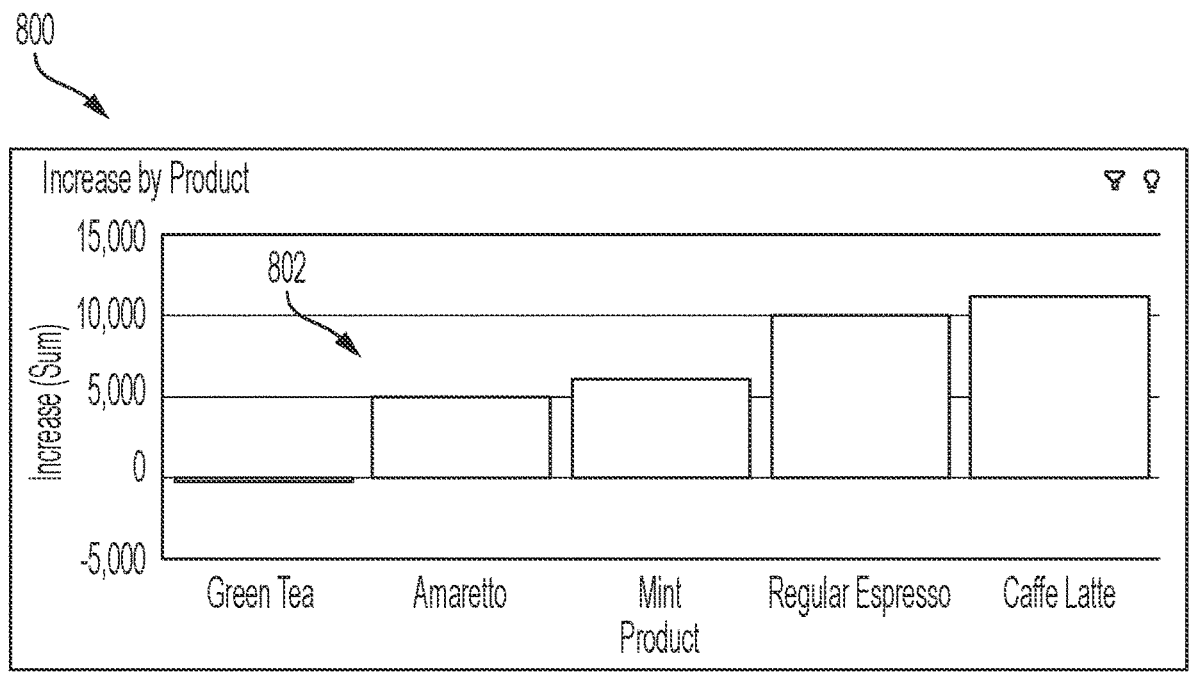
FIG. 8 illustrates an implementation example associated with a chart representing product and code identification, in accordance with embodiments of the present invention.

FIG. 8 illustrates an implementation example associated with a chart 800 representing product and code identification, in accordance with embodiments of the present invention. The chart 800 comprises information associated with product identification (for a coffee chain owner) for products 802 that are not profitable. Likewise, chart 800 presents information associated with profitability improvement for products 802. The owner may view bottom selling products within chart 800. Chart 800 presents information illustrating that profits for green tea, amaretto, and mint products are insufficient. Therefore, the coffee chain owner is enabled to compare the profit vs cost of goods (COGS) for every product using chart 800.

Figure 9:
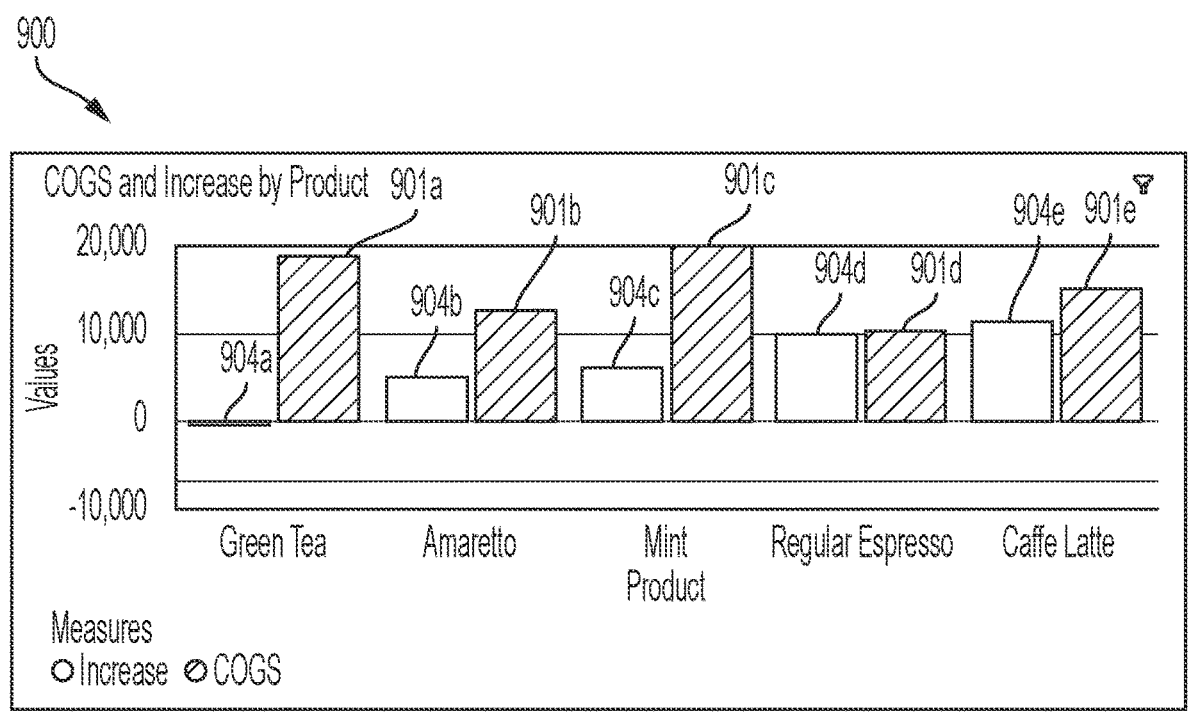
FIG. 9 illustrates a chart associated with the implementation example of FIG. 8, in accordance with embodiments of the present invention.

FIG. 9 illustrates a chart 900 associated with the implementation example of FIG. 8, in accordance with embodiments of the present invention. Chart 800 comprises information illustrating that COGS 901a, 901b, 901c, and 901e are higher than actual profits for products 904a, 904b, 904c, and 904e. Therefore, the coffee shop owner is enabled to determine actions (via code execution) for improving profitability.

Figure 10:
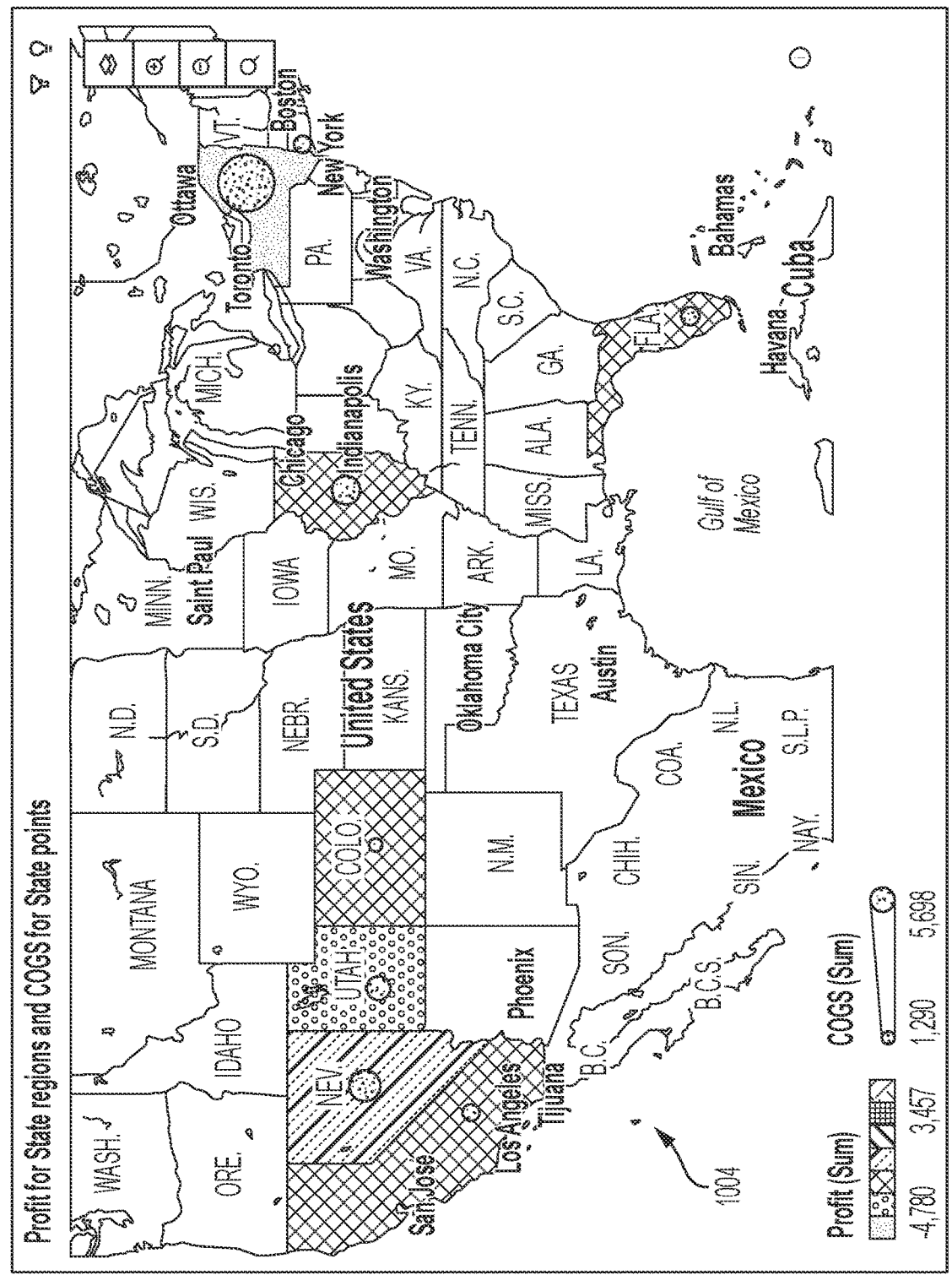
FIG. 10 illustrates a map associated with the implementation example of FIGS. 8 and 9, in accordance with embodiments of the present invention.

FIG. 10 illustrates a map 1000 associated with the implementation example of FIGS. 8 and 9, in accordance with embodiments of the present invention. Map 1000 illustrates states 1004 (within the USA) differentiated by profit and point size by with respect to COGs for mint products. Map 1000 is configured to identify key insights associated with COGs vs profit (for the mint products) within different geographical locations such that the coffee chain owner may deduce that sales are low and COGS are high in New York via a contrast between a heat of color representing profit and COGS. In contrast, Illinois illustrates an opposite scenario for the same product (i.e., mint products). Therefore, the coffee shop may travel to both states (New York and Illinois) to compare production methods and supply chain information for the mint product in Illinois and New York. Therefore, the coffee shop owner is enabled to adopt production methods deployed in Illinois for New York to reduce COGS in New York.

Figure 11:
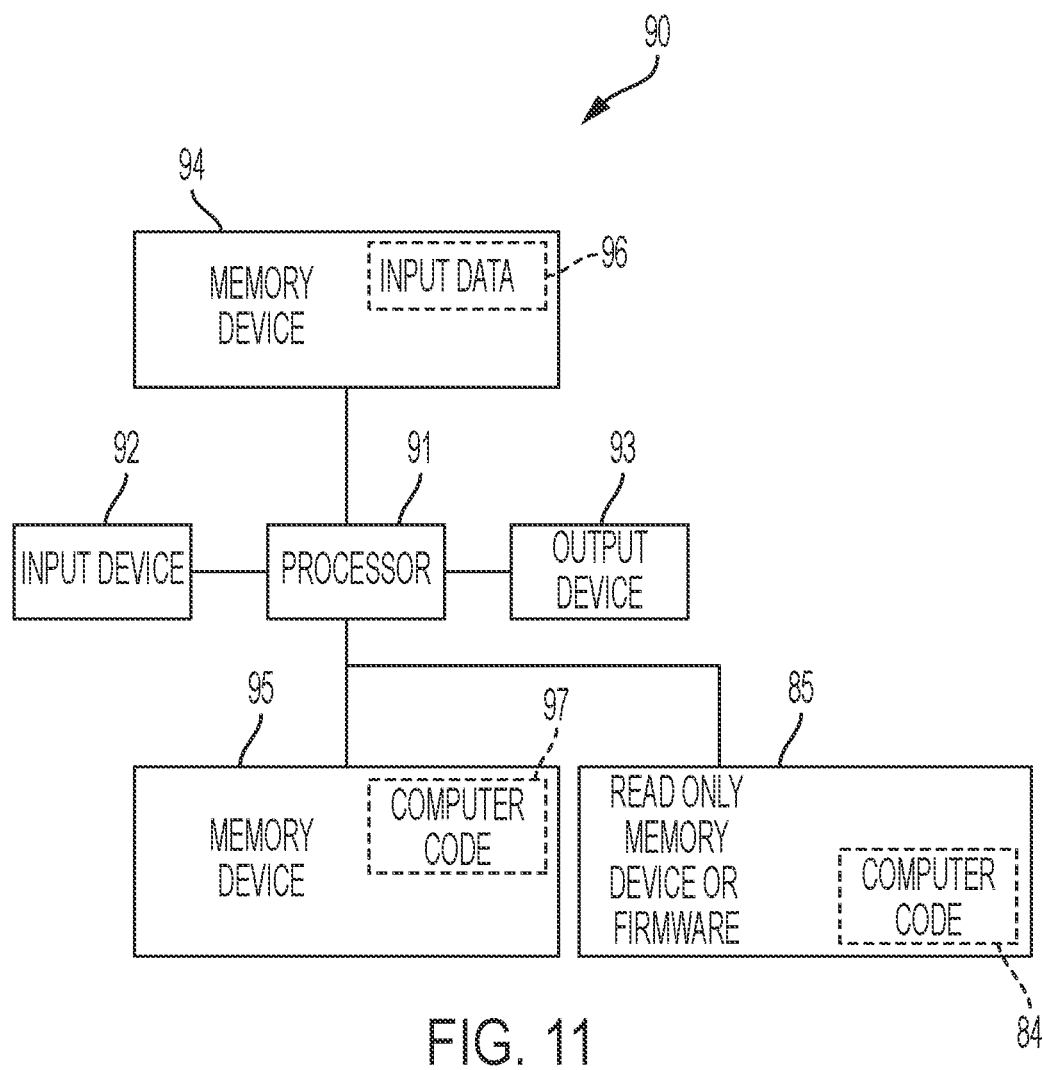
FIG. 11 illustrates a computer system used by the system of FIG. 1 for improving software technology associated with selecting visual presentations with respect to a type, executing an associated action resulting in hardware and software of a server hardware being operationally modified, and presenting the selected visual presentations, in accordance with embodiments of the present invention.

FIG. 11 illustrates a computer system 90 (e.g., server hardware 14, hardware/software sources 25, and hardware/software interface 29 of FIG. 1) used by or comprised by the system 100 of FIG. 1 for improving software technology associated with selecting visual presentations with respect to a type, executing an associated action resulting in hardware and software of a server hardware being operationally modified, and presenting the selected visual presentations, in accordance with embodiments of the present invention.

Aspects of the present invention may take the form of an entirely hardware embodiment, an entirely software embodiment (including firmware, resident software, microcode, etc.) or an embodiment combining software and hardware aspects that may all generally be referred to herein as a "circuit," "module," or "system."

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing apparatus receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++, spark, R language, or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, device (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing device to produce a machine, such that the instructions, which execute via the processor of the computer or other programmable data processing device, create means for implementing the functions/acts specified in the flowchart and/or block diagram block or blocks. These computer readable program instructions may also be stored in a computer readable storage medium that can direct a computer, a programmable data processing device, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing device, or other device to cause a series of operational steps to be performed on the computer, other programmable device or other device to produce a computer implemented process, such that the instructions which execute on the computer, other programmable device, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be accomplished as one step, executed concurrently, substantially concurrently, in a partially or wholly temporally overlapping manner, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The computer system 90 illustrated in FIG. 11 includes a processor 91, an input device 92 coupled to the processor 91, an output device 93 coupled to the processor 91, and memory devices 94 and 95 each coupled to the processor 91. The input device 92 may be, inter alia, a keyboard, a mouse, a camera, a touchscreen, etc. The output device 93 may be, inter alia, a printer, a plotter, a computer screen, a magnetic tape, a removable hard disk, a floppy disk, etc. The memory devices 94 and 95 may be, inter alia, a hard disk, a floppy disk, a magnetic tape, an optical storage such as a compact disc (CD) or a digital visual disc (DVD), a dynamic random access memory (DRAM), a read-only memory (ROM), etc. The memory device 95 includes a computer code 97. The computer code 97 includes algorithms (e.g., the algorithm of FIG. 2) for improving software technology associated with selecting visual presentations with respect to a type, executing an associated action resulting in hardware and software of a server hardware being operationally modified, and presenting the selected visual presentations. The processor 91 executes the computer code 97. The memory device 94 includes input data 96. The input data 96 includes input required by the computer code 97. The output device 93 displays output from the computer code 97. Either or both memory devices 94 and 95 (or one or more additional memory devices Such as read only memory device 96) may include algorithms (e.g., the algorithm of FIG. 2) and may be used as a computer usable medium (or a computer readable medium or a program storage device) having a computer readable program code embodied therein and/or having other data stored therein, wherein the computer readable program code includes the computer code 97. Generally, a computer program product (or, alternatively, an article of manufacture) of the computer system 90 may include the computer usable medium (or the program storage device).

In some embodiments, rather than being stored and accessed from a hard drive, optical disc or other writeable, rewriteable, or removable hardware memory device 95, stored computer program code 84 (e.g., including algorithms) may be stored on a static, nonremovable, read-only storage medium such as a Read-Only Memory (ROM) device 85, or may be accessed by processor 91 directly from such a static, nonremovable, read-only medium 85. Similarly, in some embodiments, stored computer program code 97 may be stored as computer-readable firmware 85, or may be accessed by processor 91 directly from such firmware 85, rather than from a more dynamic or removable hardware data-storage device 95, such as a hard drive or optical disc.

Still yet, any of the components of the present invention could be created, integrated, hosted, maintained, deployed, managed, serviced, etc. by a service supplier who offers to improve software technology associated with selecting visual presentations with respect to a type, executing an associated action resulting in hardware and software of a server hardware being operationally modified, and presenting the selected visual presentations. Thus, the present invention discloses a process for deploying, creating, integrating, hosting, maintaining, and/or integrating computing infrastructure, including integrating computer-readable code into the computer system 90, wherein the code in combination with the computer system 90 is capable of performing a method for enabling a process for improving software technology associated with selecting visual presentations with respect to a type, executing an associated action resulting in hardware and software of a server hardware being operationally modified, and presenting the selected visual presentations. In another embodiment, the invention provides a business method that performs the process steps of the invention on a subscription, advertising, and/or fee basis. That is, a service supplier, such as a Solution Integrator, could offer to enable a process for improving software technology associated with selecting visual presentations with respect to a type, executing an associated action resulting in hardware and software of a server hardware being operationally modified, and presenting the selected visual presentations. In this case, the service supplier can create, maintain, support, etc. a computer infrastructure that performs the process steps of the invention for one or more customers. In return, the service supplier can receive payment from the customer(s) under a subscription and/or fee agreement and/or the service supplier can receive payment from the sale of advertising content to one or more third parties.

While FIG. 11 shows the computer system 90 as a particular configuration of hardware and software, any configuration of hardware and software, as would be known to a person of ordinary skill in the art, may be utilized for the purposes stated supra in conjunction with the particular computer system 90 of FIG. 11. For example, the memory devices 94 and 95 may be portions of a single memory device rather than separate memory devices.

Cloud Computing Environment

It is to be understood that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as Follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported, providing transparency for both the provider and consumer of the utilized service.

Service Models are as Follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as Follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure that includes a network of interconnected nodes.

Figure 12:
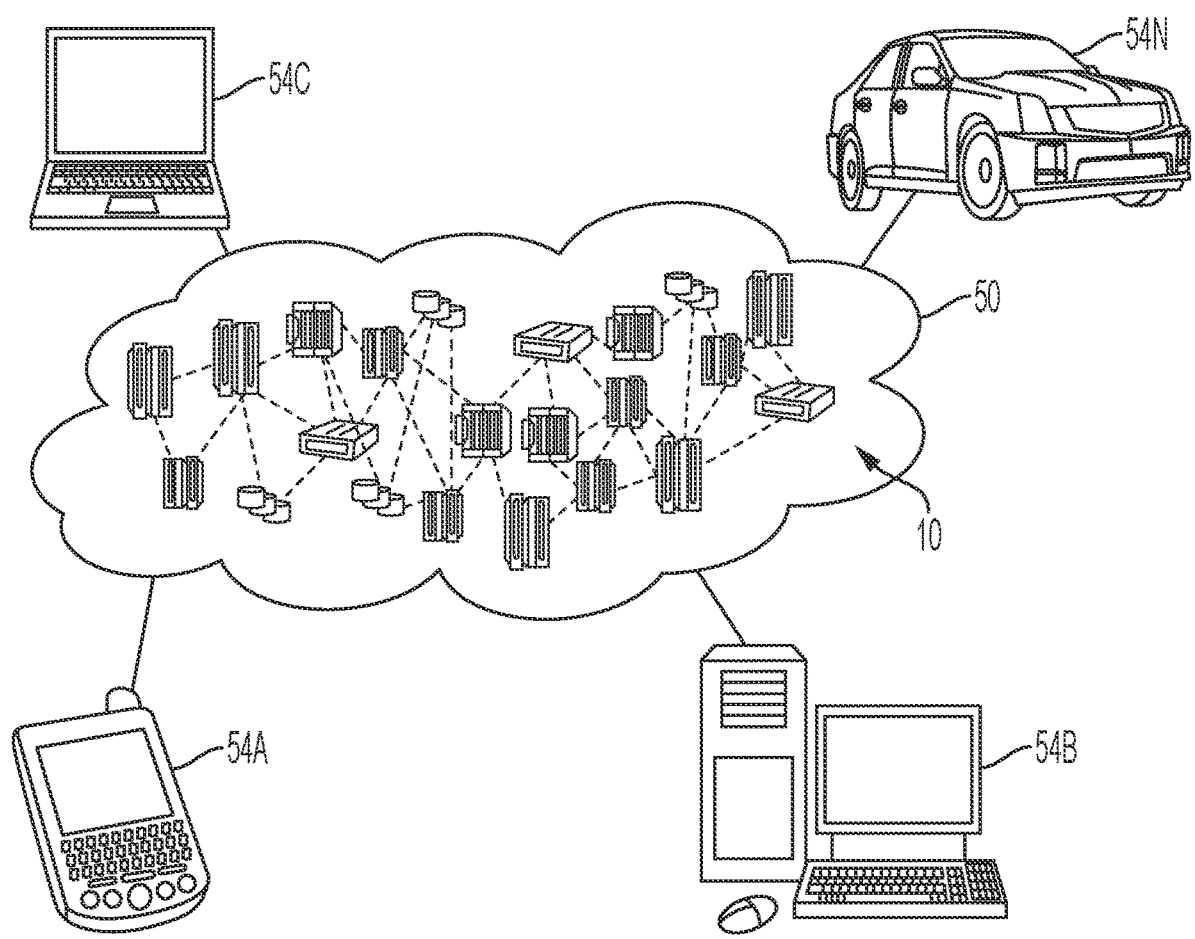
FIG. 12 illustrates a cloud computing environment, in accordance with embodiments of the present invention.

Referring now to FIG. 12, illustrative cloud computing environment 50 is depicted. As shown, cloud computing environment 50 includes one or more cloud computing nodes 10 with which local computing devices used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A, 54B, 54C and 54N shown in FIG. 12 are intended to be illustrative only and that computing nodes 10 and cloud computing environment 50 can communicate with any type of computerized device over any type of network and/or network addressable connection (e.g., using a web browser).

Figure 13:
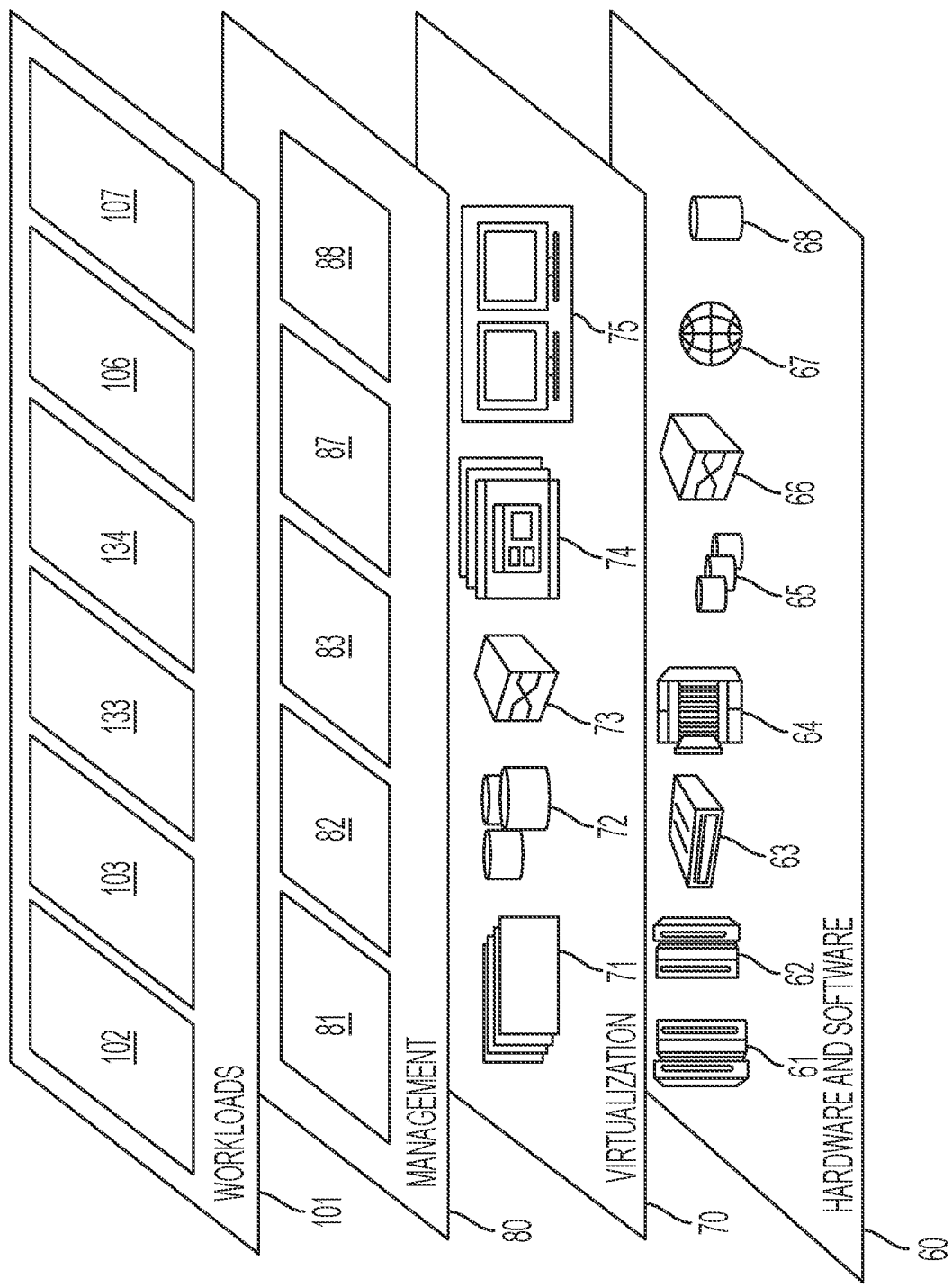
FIG. 13 illustrates a set of functional abstraction layers provided by cloud computing environment, in accordance with embodiments of the present invention.

Referring now to FIG. 13, a set of functional abstraction layers provided by cloud computing environment 50 (see FIG. 12) is shown. It should be understood in advance that the components, layers, and functions shown in FIG. 13 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may include application software licenses. Security provides identity verification for cloud consumers and tasks, as well as protection for data and other resources. User portal 83 provides access to the cloud computing environment for consumers and system administrators. Service level management 87 provides cloud computing resource allocation and management such that required service levels are met. Service Level Agreement (SLA) planning and fulfillment 88 provide pre-arrangement for, and procurement of, cloud computing resources for which a future requirement is anticipated in accordance with an SLA.

Workloads layer 101 provides examples of functionality for which the cloud computing environment may be utilized. Examples of workloads and functions which may be provided from this layer include: mapping and navigation 102; software development and lifecycle management 103; virtual classroom education delivery 133; data analytics processing 134; transaction processing 106; and for improving software technology associated with selecting visual presentations with respect to a type, executing an associated action resulting in hardware and software of a server hardware being operationally modified, and presenting the selected visual presentations 107.

While embodiments of the present invention have been described herein for purposes of illustration, many modifications and changes will become apparent to those skilled in the art. Accordingly, the appended claims are intended to encompass all such modifications and changes as fall within the true spirit and scope of this invention.

What is claimed is:

1. A code and action generation method comprising:
selecting, by a processor of a server hardware device, an unbound column from a plurality of unbound columns not bounded to any slot of any chart of a plurality of charts, wherein each unbound column is an array whose elements are binary representations of features for a visual presentation to be presented to a user;
selecting, by the processor, a chart from the plurality of charts;
selecting, by the processor, a slot from a plurality of slots in the selected chart;
receiving, by the processor from a plurality of hardware and software sources, digital description data associated with the visual presentation and one or more associated actions to be executed, wherein the visual presentation includes a visual presentation of the selected chart;
generating by the processor in response to said receiving the digital description data, a code-based class comprising executable code for each portion of the digital description data with respect to the visual presentation;
executing, by the processor, the executable code of the generated code-based class comprising executing the one or more actions including: operationally modifying hardware and software of the server hardware device and binding the selected unbound column to the selected slot of the selected chart by inputting the selected unbound column into the selected slot of the selected chart; and
after said binding, presenting, by the processor to the user via a hardware and software interface, the visual presentation.

2. The method of claim 1, wherein the visual presentation is associated with user interface based graphical presentations, and wherein the digital description data describes names, hardware and software communication slots, and statistical and ontological concept features of the visual presentation.

3. The method of claim 2, wherein the ontological and statistical concept features are associated with a network-based dictionary of concept and statistical mapping code.

4. The method of claim 1, wherein said executing the one or more actions further comprises:
modifying self learning software code in response to results of said binding the selected unbound column to the selected slot of the selected chart.

5. The method of claim 4, wherein the method further comprises prior to said modifying self learning software code:
generating, by the processor, the self learning software code for executing future processes; and
storing, by the processor, the self learning software code within a modified portion of a memory structure of the server hardware device.

6. The method of claim 1, wherein said selecting an unbound column comprises randomly selecting the unbounded column from the plurality of unbound columns.

7. The method of claim 1, wherein said selecting a chart comprises randomly selecting the chart from the plurality of charts.

8. The method of claim 1, wherein each slot of each chart has a previously assigned unit binding score measured by a comparison of the binary representations of features in the selected unbounded column with a specification of allowed features for each slot of each chart; and
wherein said selecting the chart and said selecting the slot in the selected chart comprises:
determining an overall binding score of each chart as an aggregation of the unit binding scores of the slots of each chart;
selecting the chart having a highest overall binding score; and
selecting the slot having the highest unit binding score in the selected chart.

9. The method of claim 1, wherein the method further comprises:
generating, by said processor from chart descriptors of the selected chart, reward code for the executed action, wherein the chart descriptors specify slots of the selected chart in terms of allowed features, and wherein the chart descriptors are described in a high-level software language specifying a chart name of the randomly selected chart, slots of the randomly selected chart, and both statistical and ontological concept features for the selected column bound to the slot of the selected chart.

10. The method of claim 9, wherein said generating the reward code comprises:
inputting the chart descriptors into a visual code training system; and
responding, by the visual code training system, to said binding by calculating the reward code in a manner that enables the visual code training system to be easily extensible and enables new charts to be subsequently added to the plurality of charts without excessive development efforts.

11. A computer program product, comprising a computer readable hardware storage device storing a computer readable program code, said computer readable program code comprising an algorithm that when executed by a processor of a server hardware device implements a code and action generation method, said method comprising:
selecting, by the processor, an unbound column from a plurality of unbound columns not bounded to any slot of any chart of a plurality of charts, wherein each unbound column is an array whose elements are binary representations of features for a visual presentation to be presented to a user;
selecting, by the processor, a chart from the plurality of charts;
selecting, by the processor, a slot from a plurality of slots in the selected chart;
receiving, by the processor from a plurality of hardware and software sources, digital description data associated with the visual presentation and one or more associated actions to be executed, wherein the visual presentation includes a visual presentation of the selected chart;
generating by the processor in response to said receiving the digital description data, a code-based class comprising executable code for each portion of the digital description data with respect to the visual presentation;

executing, by the processor, the executable code of the generated code-based class comprising executing the one or more actions including: operationally modifying hardware and software of the server hardware device and binding the selected unbound column to the selected slot of the selected chart by inputting the selected unbound column into the selected slot of the selected chart; and after said binding, presenting, by the processor to the user via a hardware and software interface, the visual presentation.

12. The computer program product of claim 11, wherein the visual presentation is associated with user interface based graphical presentations, and wherein the digital description data describes names, hardware and software communication slots, and statistical and ontological concept features of the visual presentation.

13. The computer program product of claim 12, wherein the ontological and statistical concept features are associated with a network-based dictionary of concept and statistical mapping code.

14. The computer program product of claim 11, wherein said executing the one or more actions comprises:

modifying self learning software code in response to results of said binding the selected unbound column to the selected slot of the selected chart.

15. The computer program product of claim 14, wherein the method further comprises prior to said modifying self learning software code:

generating, by the processor, the self learning software code for executing future processes; and storing, by the processor, the self learning software code within a modified portion of a memory structure of the server hardware device.

16. A server hardware device comprising a processor coupled to a computer-readable memory unit, said memory unit comprising instructions that when executed by the processor implements a code and action generation method comprising:

selecting, by the processor, an unbound column from a plurality of unbound columns not bounded to any slot of any chart of a plurality of charts, wherein each unbound column is an array whose elements are binary representations of for a visual presentation to be presented to a user;

selecting, by the processor, a chart from the plurality of charts;

selecting, by the processor, a slot from a plurality of slots in the selected chart;

receiving, by the processor from a plurality of hardware and software sources, digital description data associated with the visual presentation and one or more associated actions to be executed, wherein the visual presentation includes a visual presentation of the selected chart;

generating, by the processor in response to said receiving the digital description data, a code-based class comprising executable code for each portion of the digital description data with respect to the visual presentation;

executing, by the processor, the executable code of the generated code-based class comprising executing the one or more actions including: operationally modifying hardware and software of the server hardware device and binding the selected unbound column to the selected slot of the selected chart by inputting the selected unbound column into the selected slot of the selected chart; and after said binding, presenting, by the processor to the user via a hardware and software interface, the visual presentation.

17. The server hardware device of claim 16, wherein the visual presentation is associated with user interface based graphical presentations, and wherein the digital description data describes names, hardware and software communication slots, and statistical and ontological concept features of the visual presentation.

18. The server hardware device of claim 17, wherein the ontological and statistical concept features are associated with a network-based dictionary of concept and statistical mapping code.

* * * * *